United States Patent
Bae et al.

(10) Patent No.: US 9,682,152 B2
(45) Date of Patent: Jun. 20, 2017

(54) INTERFERON-ALPHA FUSION PROTEIN IN WHICH CYTOPLASMIC TRANSDUCTION PEPTIDE AND POLYETHYLENE GLYCOL ARE BONDED TO ONE ANOTHER

(71) Applicant: JW CREAGENE INC., Seongnam-si (KR)

(72) Inventors: Yong Soo Bae, Suwon-si (KR); Seung Ho Hong, Seongnam-si (KR); Young Hoon Kim, Namyangju-si (KR); Seung Soo Han, Seongnam-si (KR); Jin Kim, Seoul (KR)

(73) Assignee: JW CREAGENE INC., Seongnam-si (KR)

( * ) Notice: Subject to any disclaimer, the term of this patent is extended or adjusted under 35 U.S.C. 154(b) by 28 days.

(21) Appl. No.: 14/421,375

(22) PCT Filed: Aug. 7, 2013

(86) PCT No.: PCT/KR2013/007136
§ 371 (c)(1),
(2) Date: Feb. 12, 2015

(87) PCT Pub. No.: WO2014/027789
PCT Pub. Date: Feb. 20, 2014

(65) Prior Publication Data
US 2015/0202312 A1 Jul. 23, 2015

(30) Foreign Application Priority Data

Aug. 13, 2012 (KR) .................. 10-2012-0088610

(51) Int. Cl.
| | |
|---|---|
| *A61K 38/21* | (2006.01) |
| *A61K 39/00* | (2006.01) |
| *A61K 38/03* | (2006.01) |
| *C07K 14/56* | (2006.01) |
| *C12P 7/20* | (2006.01) |
| *A61K 47/48* | (2006.01) |
| *A61K 38/16* | (2006.01) |

(52) U.S. Cl.
CPC ........ *A61K 47/48215* (2013.01); *A61K 38/16* (2013.01); *A61K 38/212* (2013.01); *C07K 14/56* (2013.01); *C07K 2319/00* (2013.01); *C07K 2319/10* (2013.01)

(58) Field of Classification Search
None
See application file for complete search history.

(56) References Cited

U.S. PATENT DOCUMENTS

| | | | |
|---|---|---|---|
| 8,623,348 B2 * | 1/2014 | Lee ..................... | C07K 14/56 424/185.1 |
| 2008/0317714 A1 | 12/2008 | Janssen et al. | |
| 2012/0134961 A1 | 5/2012 | Lee et al. | |

FOREIGN PATENT DOCUMENTS

KR      1020050025143 A      3/2005

OTHER PUBLICATIONS

Cacciarelli et al., "Immunoregulatory cytokines in chronic hepatitis C virus infection: pre- and posttreatment with interferon alfa," Hepatology. 24(1):6-9 (1996).
Ketikoglou et al, "Extensive psoriasis induced by pegylated interferon alpha-2b treatment for chronic hepatitis B," Eur J Dermatol. 15(2):107-9 (2005).

* cited by examiner

*Primary Examiner* — Christine J Saoud
*Assistant Examiner* — Jegatheesan Seharaseyon
(74) *Attorney, Agent, or Firm* — Clark & Elbing LLP; Susan M. Michaud

(57) ABSTRACT

The present invention relates to IFN-α fusion protein in which a cytoplasmic transduction peptide (CTP) and polyethylene glycol (PEG) are bonded to an IFN-α protein. The IFN-α fusion protein of the present invention is characterized in that the specific activity of interferon remains high, the half-life of the INF-α fusion protein is extended when delivered in vivo, and the mobility of the interferon in a liver is improved. The IFN-α fusion protein of the present invention can be used in the development of protein drugs effective in preventing or treating liver diseases, including various types of viral infections or the like.

10 Claims, 6 Drawing Sheets

A. N-TERMINAL PEG ATTACHMENT

301N: 30 KD, LINEAR

DI-PEG: 30 KD x2, LINEAR

401N: 40 KD, LINEAR

202N: 20 KD x2, BRANCHED

B. INTERNAL PEG ATTACHMENT

202K: 20 KD x2, BRANCHED (2+4)K: (5 KD x2+7.5 KD x2), BRANCHED

C. C-TERMINAL PEG ATTACHMENT

401C: 40 KD, LINEAR

202C: 20 KD x2, BRANCHED

INTERFERON-ALPHA FUSION PROTEIN IN WHICH CYTOPLASMIC TRANSDUCTION PEPTIDE AND POLYETHYLENE GLYCOL ARE BONDED TO ONE ANOTHER

TECHNICAL FIELD

The present invention relates to an interferon-alpha (IFN-α) fusion protein in which a cytoplasmic transduction peptide (CTP) and polyethylene glycol are co-bound to the IFN-α protein.

BACKGROUND ART

Interferon has been used as a therapeutic agent for hepatitis, and commercialized as interferon-alpha formulations (e.g., Intron-A; Schering and Roferon-A; Roche) and PEGylated IFN formulations (e.g., PEG-Intron: Schering, Pegasys: Roche) having reduced numbers of administration than interferon-alpha formulation.

Examples of initial side effects of interferon-alpha treatment include fever, chills, asthenia universalis, anorexia, nausea and myalgia. As these symptoms appear in a dose dependent manner in most of patients, side effects are most severe at the early stage of treatment, and normally disappear after the end of treatment. Further, it has been known that frequency and severity of side effects during PEG-interferon-alpha treatment are similar to those of interferon-alpha treatment (see Kwan Sik Lee, Dong Joon Kim et al. Management of Chronic Hepatitis B, The *Korean Journal of Hepatology*. 13:447-488, (2007)).

As above, since side effects depending on administration dose of interferon have been known, reduction in administration dose is required to minimize side effects when interferon is used as a therapeutic agent.

Conventionally, to solve problems described above, a cytoplasmic transduction peptide (CTP) is fused with interferon thereby improving an ability of interferon to migrate into liver to provide a tool for resolving side effects of interferon alpha treatment. However, when the fusion protein is administered to a mouse model, the initial activity is rapidly decreased such that at least half of the activity is decreased after 6 hours. Thus, a need has been emerged to improve the retention property and the ability to migrate to liver of the fusion protein.

Throughout the specification, numerous journals and patent documents are referenced, and the citation is indicated. Disclosures of cited journals and patent documents are incorporated herein in their entireties by reference to more clearly describe the level of the technical field to which the present invention belongs and features of the present invention.

DISCLOSURE OF THE INVENTION

Technical Problem

The present inventors have been studied and tried to develop an interferon-alpha fusion protein having improved pharmaceutical efficacy than that of conventional interferon through a protein modification such as binding between a heterogenous peptide and polyethylene glycol. Consequently, the present invention is completed by experimentally demonstrating that: when a cytoplasmic transduction peptide (CTP) is bound to an N-terminal of the interferon alpha protein through a linker while polyethylene glycol is bound to a C-terminal thereof through a linker at the same time, the intrinsic activity of interferon remains high; in vivo half-life is extended; and an ability to migrate into liver is enhanced.

One object of the present invention is to provide an interferon-alpha fusion protein in which reduction in administration dose of interferon may be expected by improving the ability to migrate to liver and the retention property of the conventional interferon fusion protein.

Another object of the present invention is to provide a nucleic acid molecule coding the interferon-alpha fusion protein.

Still another object of the present invention is to provide a transformant including the nucleic acid molecule.

Even another object of the present invention is to provide a method for preparing the interferon-alpha fusion protein.

Yet another object of the present invention is to provide a pharmaceutical composition for preventing or treating liver diseases.

Objects and benefits of the present invention will be apparent by appended detailed description of the invention, claims, and drawings.

Technical Solution

According to one aspect of the present invention, the present invention provides an interferon-alpha fusion protein expressed by CTP-X-IFNα-Y-PEG, wherein the CTP is a cytoplasmic transduction peptide; the X is a peptide linker including 1 to 10 glycines; the Y is a peptide linker including 1 to 100 cysteines, glycines, or combinations of glycine and cysteine; the IFNα is interferon-alpha 2a or interferon-alpha 2b; and the PEG is polyethylene glycol.

The present inventors have been studied and tried to develop an interferon-alpha fusion protein having improved pharmaceutical efficacy than that of conventional interferon through a protein modification such as binding between a heterogenous peptide and polyethylene glycol. In one example of the present invention, a linker is introduced between an interferon-alpha protein and CTP. Then, a linker, which does not alter a structure of the interferon-alpha protein, is selected, and polyethylene glycol is fused to a C-terminal of the fusion protein. Thereafter, an activity of the fusion protein is analyzed.

Consequently, when the cytoplasmic transduction peptide (CTP) is bound to an N-terminal of the interferon alpha protein through a linker while polyethylene glycol is bound to the C-terminal through a linker, it has been experimentally proven that: the intrinsic activity of interferon remains high; in vivo half-life is extended; and an ability to migrate into liver is enhanced. In other word, the result primarily demonstrates that the in vivo motility and retention property of the fusion protein are improved by respectively binding CTP and PEG to N and C terminals of the interferon-alpha protein through a linker which improves the therapeutic effect of the conventional fusion protein to which PEG or both PEG and CTP are bound. Specifically, such effect may be achieved by: 1) optimizing a function of CTP by binding CTP to the interferon alpha protein through a linker; 2) extending in vivo half-life by fusing polyethylene glycol to C-terminal of the interferon-alpha protein; and 3) linking polyethylene glycol in a linear form at the C-terminal of the interferon-alpha protein.

As used herein, the term "interferon-alpha (IFNα) fusion protein" means an interferon-alpha protein to which only CTP is bound or both CTP and PEG are simultaneously bound. Herein, when referring to a fusion protein of the interferon-alpha protein to which only CTP is bound, it is expressed by "CTP-X-IFNα-Y" as well.

As used herein, the term "cytoplasmic transduction peptide (CTP)" is a newly-coined word made by the present inventors, and means a peptide which has a property of remaining in cytoplasm while retaining an ability to penetrate cell membrane, that is, a property of suppressing migration into a nucleus.

CTP included in the IFNα fusion protein of the present invention is a delivery peptide developed by the present inventors to resolve problems of PTD and filed and registered (Korean Patent No. 0608558, U.S. Pat. No. 7,101,844, and Japan Patent No. 4188909), and details regarding CTP disclosed in these patent literatures are incorporated herein by reference.

For CTP included in the IFNα fusion protein of the present invention, a length of a peptide corresponds to a length generally accepted in the art, and is preferably 9 to 20 amino acids, more preferably 9 to 15 amino acids, and most preferably 11 amino acids.

According to a preferred example of the present invention, CTP included in the IFNα fusion protein of the present invention includes an amino acid sequence selected from the group consisting of sequences expressed by SEQ ID NOs: 1 to 14. Preferably, in the present invention, CTP includes the sequence of SEQ ID NO: 1.

CTP has its own distinctive properties, that is, an excellent ability to penetrate cell membrane; in vivo cytotoxicity lower than other delivery systems (in particular, a protein transduction domain (PTD) or polyarginine)) due to the property of inhibiting migration into a nucleus after introduction into cells; and transferring the fused protein to liver. Thus, CTP is an effective drug delivery peptide for treating diseases targeting liver.

As used herein, the term "interferon-alpha (IFNα)" means a species-specific protein group having high homogeneity which inhibits viral replication and cell proliferation and regulates immune-response.

IFNα included in the IFNα fusion protein of the present invention is recombinant IFNα 2b, recombinant IFNα 2a, recombinant IFNα 2c, IFNα-n1 (which is a purified mixture of natural alpha-interferon), consensus alpha-interferon (see U.S. Pat. Nos. 4,897,471 and 4,695,623) or IFNα-n3 (which is a mixture of natural alpha-interferon), more preferably IFNα 2a or IFNα 2b, and the most preferably IFNα 2b. A method for preparing IFNα 2b is described in U.S. Pat. No. 4,530,901.

According to a preferred example of the present invention, IFNα included in the IFNα fusion protein of the present invention includes the amino acid sequence expressed by SEQ ID NO: 21.

In the IFNα fusion protein of the present invention, the X is a peptide linker including 1 to 10 glycine residues. CTP is bound to the N-terminal of IFNα through the peptide linker.

By linking CTP and IFNα with the peptide linker X, the CTP peptide become flexible and freely rotatable so that the intrinsic function of CTP may be facilitated.

In addition, during expression and purification of a CTP-bound fusion protein, precipitation of the fusion protein is minimized due to hydrophobicity of CTP, and purification yield may thus be increased.

According to one specific example of the present invention, precipitation is formed during purification of a CFN1 protein (CTP-IFNα), while precipitation is not formed during purification of a CFN8 protein (CTP-GGGG-IFNα) to which the peptide linker is bound.

Preferably, the peptide linker X may be 1 to 10 glycine residues, preferably 1 to 8 glycine residues, more preferably 1 to 7 glycine residues, still more preferably 1 to 5 glycine resides, even more preferably 3 to 5 glycines residues, and 4 residues.

In the IFNα fusion protein of the present invention, the Y is a peptide linker including 1 to 100 cysteine residues, or glycine residues, or combinations of glycine and cysteine residues. Through the peptide linker, PEG is bound to the C-terminal of IFNα. The peptide linker Y may include 0 to 10 glycine residues and 1 to 80 cysteine residues, more preferably 0 to 10 glycine residues and 1 to 60 cysteine residues, further more preferably 1 to 10 glycine residues and 1 to 10 cysteine residues, and still more preferably 1 to 5 glycine residues and 1 to 5 cysteine residues. Also, the peptide linker Y may include 0 to 10 glycine residue or 1 to 80 cysteine residues, more preferably 1 to 10 glycine residues or 1 to 60 cysteine residues, further more preferably 1 to 10 glycine residues or 1 to 10 cysteine residues, sill more preferably 1 to 5 glycine residues or 1 to 5 cysteine residue, and the most preferably 3 to 5 glycine residues or 3 to 5 cysteine residue.

According to a preferred example of the present invention, in the IFNα fusion protein of the present invention, a peptide moiety expressed by "CTP-X-IFNα-Y" is a peptide including an amino acid sequence selected from the group consisting of sequences expressed by SEQ ID NOs: 15 to 20, and more preferably, a peptide formed by the amino acid sequence of SEQ ID No: 18.

In the present invention, it is understood that the amino acid sequence of the peptide moiety expressed by "CTP-X-IFNα-Y" includes an amino acid sequence having substantial homogeneity with any one of amino acid sequences of SEQ ID NOs: 15 to 20. By the substantial homogeneity, it is meant an amino acid sequence showing at least 80% of homogeneity, more preferably at least 90% of homogeneity, and the most preferably at least 95% of homogeneity in the case where the amino acid sequence of the present invention as described above is aligned with any other sequences to maximally correspond, and then the aligned sequences are analyzed by using the algorism conventionally used in the art.

PEG is bound to the C-terminal of the IFNα fusion protein of the present invention.

It is undesirable that PEG is bound to the N-terminal of the IFNα fusion protein of the present invention because abilities of CTP to penetrate cell membrane and to migrate to liver are hindered. In other word, as demonstrated by one specific example of the present invention below, when PEG is bound to the N-terminal of the IFNα fusion protein, although the in vitro antiviral activity and stability in blood are excellent, the ability to migrate to liver is significantly declined.

PEG reduces renal clearance mechanism to thereby extend the blood half-life, and thus PEG shows an effect of reducing administration does of the fusion protein of the present invention.

According to a preferred example of the present invention, molecular weight of the PEG may be 20 to 60 kDa, more preferably 20 to 50 kDa, still more preferably 30 to 45 kDa, even more preferably 35 to 45 kDa, and the most preferably 40 to 45 kDa. When 40 to 45 kDa of PEG is used, the highest increase in the ability to migrate to liver is showed.

According to another preferred example of the present invention, the PEG may be linear PEG or branched PEG.

As used herein, the term "linear PEG" means PEG in a form of a single chain without a branch, and the term "branched PEG" means a form in which 2 to 10 PEG chains are branched out from a central core group.

The PEG of the present invention is linear PEG to which a particular amino acid residue of the interferon alpha protein is bound. Thus, the finally produced PEG-interferon alpha fusion protein is easily separated and purified, and also there is an advantage in quality control of the protein.

The PEGylation to bind the PEG to the IFNα fusion protein of the present invention may be performed by the method known in the art (see M. J. Roberts, M. D. Bentley et al., Chemistry for peptide and protein PEGylation, *Advanced Drug Delivery Reviews* 54:459476(2002); Francesco M., Peptide and protein PEGylation: a review of problems and solutions, *Veronese Biomaterials* 22:405-417 (2001)).

According to another aspect of the present invention, the present invention provides a nucleic acid molecule coding the peptide moiety expressed by "CTP-X-IFNα-Y" in the IFNα fusion protein of the present invention as described above.

As used herein, the term "nucleic acid molecule" comprehensively includes DNA (gDNA and cDNA) and RNA molecules, and a nucleotide, which is a fundamental constitutive unit of the nucleic acid molecule, includes a natural nucleotide, as well as, an analogue in which a sugar or a base moiety is modified (see Scheit, *Nucleotide Analogs*, John Wiley, New York (1980); Uhlman and Peyman, *Chemical Reviews*, 90:543-584(1990)).

According to a preferred example of the present invention, the nucleic acid molecule coding the peptide moiety expressed by "CTP-X-IFNα-Y" in the IFNα fusion protein of the present invention is a nucleic acid molecule coding a peptide formed by any one of amino acid sequences of SEQ ID NOs: 15 to 20, more preferably a nucleic acid molecule coding a peptide formed by the amino acid sequence of SEQ ID No: 18, and the most preferably a nucleic acid molecule having the DNA base sequence of SEQ ID No: 22.

According to another aspect of the present invention, the present invention provides a vector including the nucleic acid molecule coding the peptide moiety expressed by "CTP-X-IFNα-Y" in the IFN-α fusion protein.

The vector system of the present invention may be constructed by various methods known in the art, and the specific methods are described in Sambrook et al., *Molecular Cloning, A Laboratory Manual*, Cold Spring Harbor Laboratory Press (2001) which is incorporated herein by reference.

The vector of the present invention, typically, is constructed as a vector for cloning or expression. Further, the vector of the present invention may be constructed using prokaryotic cells or eukaryotic cells as a host. It is preferable that the nucleotide sequence of the present invention is derived from prokaryotic cells, and prokaryotic cells are used as a host in the light of convenience of culture.

When the vector of the present invention is an expression vector, and prokaryotic cells are used as a host, generally, the vector includes a strong promoter to proceed transcription (e.g., tac promoter, lac promoter, lacUV5 promoter, lpp promoter, pLλ promoter, pRλ promoter, rac5 promoter, amp promoter, recA promoter, SP6 promoter, trp promoter and T7 promoter), a ribosomal binding site to initiate translation, and transcription/translation termination sequences. When *E. coli* is used as host cells, promoter and operator sites of *E. coli* tryptophan biosynthesis (see Yanofsky, C., *J. Bacteriol.*, 158:1018-1024(1984)), and left side promoter of λ phage (pLλ promoter, see Herskowitz, I. and Hagen, D., *Ann. Rev. Genet.*, 14:399-445(1980)) may be used as a regulatory site.

The vector, which may be used in the present invention, may be constructed by manipulating a plasmid (e.g., pSC101, ColE1, pBR322, pUC8/9, pHC79, pUC19, and pET), a phage (e.g., λgt4λB, λ-Charon, λΔz1 and M13) or a virus (e.g., SV40) often used in the art.

In the case where the vector of the present invention is an expression vector, and eukaryotic cells are used as a host, a promoter derived from a genome of mammalian cells (e.g., metallothionein promoter) or a promoter derived from a mammalian virus (e.g., adenovirus late promoter, vaccinia virus 7.5 k promoter, SV40 promoter, cytomegalovirus promoter and tk promoter of HSV) may be used. The promoters generally have polyadenylation sequence as a transcription termination sequence.

To facilitate purification of the peptide expressed by "CTP-X-IFNα-Y" of the IFNα fusion protein of the present invention expressed from the vector of the present invention, fusion with other sequences may be made as necessary. The sequence to be used for fusion may be, for example, but not limited to, glutathione S-transferase (Pharmacia, USA), maltose-binding protein (NEB, USA), FLAG (IBI, USA) and 6×His (hexahistidine; Quiagen, USA).

According to preferred example of the present invention, the peptide expressed by "CTP-X-IFNα-Y" expressed by the vector of the present invention is purified by cation-exchange chromatography and gel filtration chromatography.

Further, the expression vector of the present invention may be include, as a selection marker, an antibiotic resistance gene typically used in the art which includes, for example, resistance genes to ampicillin, gentamicin, carbenicillin, chloramphenicol, streptomycin, kanamycin, geneticin, neomycin, and tetracycline.

According to another aspect of the present invention, the present invention provides a transformant including the vector of the present invention as described above.

As a host cell which may stably and constitutively express the vector of the present invention, any one of host cells known in the art may be used, examples of which include *E. coli* JM109, *E. coli* BL21 (DE3), *E. coli* RR1, *E. coli* LE392, *E. coli* B, *E. coli* X 1776, *E. coli* W3110, *Bacillus.* Sp. such as *Bacillus subtilis*, and *Bacillus thuringiensis*, and Enterobacteriacea strains such as *Salmonella typhimurium, Serratia marcescens* and various *Pseudomonas* sp.

In addition, when eukaryotic cells are transformed with the vector of the present invention, yeast (e.g., *Saccharomyce cerevisiae*), insect cells and human cells (e.g., Chinese hamster ovary (CHO) cell line, W138, BHK, COS-7, 293, HepG2, 3T3, RIN and MDCK cell lines) may be used as a host cell.

When the host cell is a prokaryotic cell, transfer of the vector of the present invention may be performed by the method as follows: the $CaCl_2$ method (see Cohen, S. N. et al., *Proc. Natl. Acac. Sci. USA*, 9:2110-2114(1973)); the Hanahan method (see Cohen, S. N. et al., *Proc. Natl. Acac. Sci. USA*, 9:2110-2114(1973); and Hanahan, D., *J. Mol. Biol.*, 166:557-580(1983)); and electroporation (see Dower, W. J. et al., *Nucleic. Acids Res.*, 16:6127-6145(1988)). Further, when the host cell is a eukaryotic cell, the vector may be introduced into the host cell by microinjection (see Capecchi, M. R., *Cell*, 22:479(1980)), calcium phosphate precipitation (see Graham, F. L. et al., *Virology*, 52:456 (1973)), electroporation (see Neumann, E. et al., *EMBO J.*, 1:841(1982)), liposome-mediated transfection (see Wong, T.

K. et al., *Gene,* 10:87(1980)), DEAE-dextran treatment (see Gopal, *Mol. Cell Biol.,* 5:1188-1190(1985)), and gene bombardment (see Yang et al., *Proc. Natl. Acad. Sci.,* 87:9568-9572(1990)).

The vector introduced into a host cell may be expressed in the host cell, and a large amount of the "CTP-X-IFNα-Y" peptide may be obtained. For example, when the expression vector includes the lac promoter, gene expression may be induced by treating the host cell with IPTG.

Hereinafter, since a method for preparing the IFNα fusion protein of the present invention includes a method for preparing the peptide expressed by "CTP-X-IFNα-Y" of the present invention as described above, the features common to both methods are not described herein to avoid excessive complexity in the specification.

According to another aspect of the present invention, the present invention provides a method for preparing the IFNα fusion protein of the present invention, the method including: (a) culturing a transformant transformed by an expression vector including the nucleic acid molecule coding the peptide moiety expressed by "CTP-X-IFNα-Y" operatively linked to a promoter; (b) obtaining a fusion protein from the culture medium of the transformant in step (a); and (c) binding PEG to a C-terminal of the fusion protein obtained in step (b).

As used herein, the term "promoter" means a DNA base sequence which regulates expression of a coding sequence or a function RNA.

As used herein, the term "operatively linked to" means a functional binding between a regulatory sequence of nucleic acid expression (for example, a promoter, a signal sequence, or an array at a transcription regulatory factor binding site) with other nucleic acid sequences, and the regulatory sequence thus regulates transcription and/or translation of the other nucleic acid sequences.

As used herein, culture of a transformant is performed by the method of culturing prokaryotic cells or eukaryotic cells known in the art. For example, any natural medium or synthetic medium may be used for culture of a transformant as long as the medium includes a carbon source, a nitrogen source, and a mineral salt which can be effectively used by prokaryotic cells or eukaryotic cells.

Culture of the transformant is typically performed under an aerobic condition such as through shaking culture or through rotation by a rotator. Temperature of culture is preferably 15 to 50° C., and period of culture is generally 5 hours to 7 days. pH of a medium is preferably maintained within a range of 3.0 to 9.0. pH of the medium is adjusted by an inorganic or an organic acid, an alkali solution, urea, calcium carbonate, and ammonia. During culture, an antibiotic such as ampicillin and tetracycline may be added as necessary.

In the present invention, the method of separating and purifying of a protein typically used in the art may be used as a method for separating a heterogeneous recombinant protein expressed from the cultured transformant cell. Examples of various available methods include solubility fractionation using ammonium sulfate or PEG, ultrafiltration separation depending on molecular weight, various chromatography (which is manufactured for separation depending on the size, charge, hydrophobicity, or affinity). Typically, combination of the method as described above is used for separation and purification.

According to another aspect of the present invention, the present invention provides a pharmaceutical composition for preventing or treating liver diseases, the composition including: (a) a pharmaceutically effective amount of the IFNα fusion protein of the present invention as described above; and (b) a pharmaceutically acceptable carrier.

Liver diseases to be treated or prevented by the composition of the present invention include liver cancer, hepatitis, liver cirrhosis and other liver diseases, and preferably liver cancer and hepatitis. For example, the hepatitis may be acute viral hepatitis, chronic hepatitis, fulminant hepatitis, more preferably hepatitis type B or C, and the most preferably hepatitis type C caused by hepatitis C virus (HCV).

According to a preferred example of the present invention, preferably, the pharmaceutical composition for treating liver diseases of the present invention may be administered parenterally, and more preferably be administered subcutaneously.

As used herein, the term "pharmaceutically effective amount" means an amount sufficient to achieve efficacy or the activity of the fusion protein of the present invention as described above.

The pharmaceutical composition of the present invention may be administered orally, parenterally, rectally, or topically, or by an inhale spray, and preferably administered parenterally as a unit dosage form containing a pharmaceutically acceptable conventional nontoxic carrier, adjuvant, and an excipient as necessary. Topical administration may include transdermal administration such as a transdermal patch, or those using iontophoresis.

As used herein, the term "parenteral administration" includes subcutaneous injection, intravenous, intramuscular, intrasternal injection or infusion technique. The drug formulation is described, for example, in the document (Hoover, John E., Remington's Pharmaceutical Sciences, Mack Publishing Co., Easton, Pa., 1975). Contents about the drug formulation are also described in the document [Liberman, H. A. and Lachman, L., Eds., Pharmaceutical Dosage Forms, Marcel Decker, New York, N.Y., 1980].

A pharmaceutically acceptable carrier, which is included in the pharmaceutical composition of the present invention, is one typically used in drug preparation and includes, but not limited to, lactose, dextrose, sucrose, sorbitol, mannitol, starch, *acacia* rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, cyclodextrin and mineral oil. The pharmaceutical composition of the present disclosure may further include a lubricant, a humectant, a sweetening agent, a favoring agent, an emulsifier, a suspending agent, and a preserving agent besides the components above. A suitable pharmaceutically acceptable carrier and a formulation are described in *Remington's Pharmaceutical Sciences* (19th ed., 1995).

Suitable administration dose of the pharmaceutical composition of the present invention may be differentially prescribed depending on various factors such as a method for formulation, a mode of administration, age, weight, sex, disease states and dietary of patients, time of administration, a route of administration, a secretion rate and reaction susceptibility. Preferably, administration dose of the pharmaceutical composition of the present invention may be 0.001 to 100 μg/kg (body weight) based on adults.

The pharmaceutical composition of the present invention is prepared in a unit dosage form by being formulated using a pharmaceutically acceptable carrier and/or excipient, or prepared by being incorporated into a multi-dose container, according to a method by which a person with ordinary skill in the technical field to which the present invention belongs could easily carry out. In this case, the formulation may be a form of a solution, suspension, syrup or emulsion in an oil or an aqueous medium, extract, fine powder, powder, granule, tablet, or capsule form, and may further include a dispersing agent or a stabilizer.

Advantageous Effects

Advantages and effects of the present invention are summarized as follow:

(i) The present invention relates to an IFNα fusion protein in which a cytoplasmic transduction peptide (CTP) and polyethylene glycol (PEG) are bounded to an IFNα protein;

(ii) The intrinsic activity of IFNα is maintained high in the IFNα fusion protein of the present invention;

(iii) For the IFNα fusion protein of the present invention, the half-life is extended, and an ability to migrate to liver is improved when administered in vivo; and (iv) The IFNα fusion protein of the present invention can be used to develop protein drugs effective in prevention or treatment of liver diseases including various viral infection.

MODE FOR CARRYING OUT THE INVENTION

Figure 1:
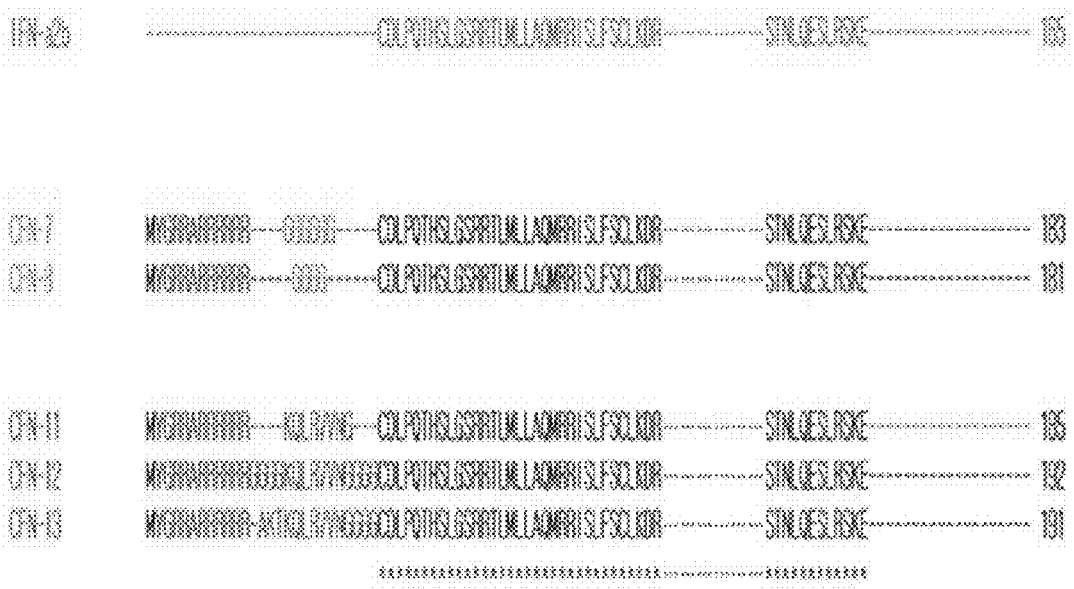
FIG. 1 shows a structure of the IFNα fusion protein of the present invention having CTP which is bound by a linker. Expressed are structures of CFN7 (CTP-GGGGGG-IFNα, SEQ. ID No: 32), CFN8 (CTP-GGGG-IFNα, SEQ. ID No: 33), CFN11 (SEQ. ID No: 34) having a hepsin cleavage linker inserted thereto, CFN12 (SEQ. ID No: 35), and CFN13 (SEQ. ID No: 36). IFN-a2b sequences (SEQ ID Nos: 37 and 38) are shown at the top of the figure.

Hereinafter, the present invention will be described in more detail with reference to examples. These examples are provided to only specifically describe the present invention, and it will be obvious to a person skilled in the art that the scope of the present invention is not limited to the examples according to the essential features of the present invention.

EXAMPLE

Example 1: Synthesis of CTP Fusion IFNα Gene Through Polymerase Chain Reaction (PCR)

A CTP peptide was inserted to an N-terminal of human-derived Interferon-α (IFNα), and a glycine linker including 4 or 6 glycines was inserted between CTP and IFNα. By using the glycine linker to link CTP and IFNα, flexibility was imparted to the CTP peptide so that a function of CTP peptide was facilitated, and precipitation during purification due to hydrophobic CTP was minimized. In addition, by inserting cysteine to a C-terminal of the IFNα gene through the PCR method, PEG may be attached to the C-terminal through a maleimide PEG reaction. In vivo half-life may be significantly increased by attaching linear PEG to the C-terminal.

At first, to insert the glycine linker between IFNα and the CTP peptide attached to the N-terminal of IFNα, PCR was performed by using the primer described in Table 1 below.

A first PCR was performed by using PR2 and PR3 primers and IFNα as a template. A second PCR was performed by using PR1 and PR2 primers and the produced PCR product as a template again. A final product thus obtained was a nucleic acid molecule coding the peptide CTP-GGGGGG-IFNα to which a linker including six glycines was linked. The final product, i.e., the CTP-GGGGGG-IFNα protein was named as CFN7 (SEQ ID NO: 32).

A first PCR was performed by using PR2 and PR4 primers and IFNα as a template. A second PCR was performed by using PR1 and PR2 primers and the produced PCR product, as a template again. A final product thus obtained was a nucleic acid molecule coding CTP-GGGG-IFNα to which a linker including four glycines was linked. The final product, i.e., the CTP-GGGG-IFNα protein was named as CFN8 (SEQ ID NO: 33).

To insert a hepsin cleavage sequence between IFNα and the CTP peptide attached to the N-terminal of IFNα, PCR was performed by using the primer described in Table 1 below. A first PCR was performed by using PR2 and PR5 primers and IFNα as a template. A second PCR was performed by using PR1 and PR2 primers and the produced PCR product, as a template again. A final product thus obtained was a nucleic acid molecule coding CTP-KQLRV-VNG-IFNα which was a peptide to which a linker including the hepsin cleavage sequence was linked. The final product, i.e., the CTP-KQLRVVNG-IFNα protein was named as CFN11 (SEQ ID NO: 34).

To co-insert glycine and the hepsin cleavage sequence between IFNα and the CTP peptide attached to the N-terminal of IFNα, PCR was performed by using the primer described in Table 1 below. A first PCR was performed by using PR2 and PR7 primers and IFNα, as a template. A second PCR was performed by using PR1 and PR2 primers and the produced PCR product, as a template again. A final product thus obtained was a nucleic acid molecule coding the peptide CTP-GGGGKQLRVVNGGGG-IFNα in which linkers respectively including four glycines and three glycines were linked at both sides of the hepsin cleavage sequence. The final product, i.e., the CTP-GGGGKQLRV-VNGGGG-IFNα protein was named as CFN12 (SEQ ID NO: 35).

To co-insert glycine and a hepatocyte growth factor activator between IFNα and the CTP peptide attached to the N-terminal of IFNα, PCR was performed by using primers described in Table 1 below. A first PCR was performed by using PR2 and PR8 primers and IFNα as a template. A second PCR was performed by using PR1 and PR2 primers and the produced PCR product as a template again. A final product thus obtained was a nucleic acid molecule coding CTP-AKTKQLRVVNGGGG-IFNα which was a peptide to which a linker including the hepatocyte growth factor activator and three glycines was linked. The final product i.e., the CTP-AKTKQLRVVNGGGG-IFNα protein was named as CFN13 (SEQ ID No: 36).

Structures of CFN7, CFN8, CFN11, CFN12, and CFN13 thus constructed were shown in FIG. 1.

TABLE 1

| Primer name | Base sequence of primer | SEQ ID. NO. | Note |
|---|---|---|---|
| PR1 | 5'-TAA TCT AGA AAA AAC CAA GGA GGT AAT AAC ATA TGT ATG GTC GTC GTG CAC GT - 3' | 23 | |
| PR2 | 5'-CAA GGA TCC CTC GAG CTA TTA TTC TTT GCT ACG CAG GCT - 3' | 24 | |
| PR3 | 5'-TAT GGT CGT CGT GCA CGT CGT CGT CGT CGT CGT GGT GGT GGT GGT GGT GGT TGC GAT CTG CCG CAG ACC - 3' | 25 | CFN7 |
| PR4 | 5'-TAT GGT CGT CGT GCA CGT CGT CGT CGT CGT CGT GGT GGT GGT GGT TGC GAT CTG CCG CAG ACC - 3' | 26 | CFN8 |
| PR5 | 5'-TAT GGT CGT CGT GCA CGT CGT CGT CGT CGT CGT aaa CAG CTG CGT GTG GTG AAC GGT TGC GAT CTG CCG CAG ACC-3' | 27 | CFN11 |
| PR6 | 5'-TAT GGT CGT CGT GCA CGT CGT CGT CGT CGT CGT GGT GGT GGT GGT AAA CAG CTG CGT GTG GTG AAC GGT GGT GGT GGT TGC GAT CTG CCG CAG ACC-5' | 28 | CFN12 |
| PR7 | 5'-TAT GGT CGT CGT GCA CGT CGT CGT CGT CGT CGT GCA AAA ACC AAA CAG CTG CGT GTG GTG AAC GGT GGT GGT GGT TGC GAT CTG CCG CAG ACC-5' | 29 | CFN13 |

Then, PCR was performed to insert cysteine to the C-terminal. A final product thus obtained was a nucleic acid molecule coding CTP-GGGG-IFNα-C in which cysteine was inserted to the C-terminal of the CTP-GGGG-IFNα gene by using PR8 and PR9 primers and CTP-GGGG-IFNα having a glycine linker of 4 glycines linked thereto as a template. The final product, i.e., the CTP-GGGG-IFNα-C protein was named as CFN8C (SEQ ID NO: 18).

TABLE 2

| Primer name | Base sequence of primer | SEQ ID. NO. | Note |
|---|---|---|---|
| PR8 | 5'-C TAG TCT AGA AAA AAC CAA GGA GGT AAT AAC ATA TGT ATG-3' | 30 | |
| PR9 | 5'-CGC GGA TCC CTA TTA GCA ACC ACC ACC ACC TTC TTT GCT ACG CAG GCT TTC TTG C-3' | 31 | CFN8C |

Example 2: Preparation of E. coli Expression Vector of Interferon-Alpha Fusion Protein To express, in E. coli, genes respectively coding CFN7 (CTP-GGGGGG-IFNα), CFN8 (CTP-GGGG-IFNα), CFN8C (CTP-GGGG-IFNα-C), CFN11 (CTP-KQLRV-VNG-IFNα), CFN12 (CTP-GGGGKQLRVVNGGGG-IFNα), and CFN13 (CTP-AKTKQLRVVNGGGG-IFNα) obtained by PCR, genes were respectively cloned to pCFM536s, which is an E. coli expression vector, to construct pCFM536-CFN7, pCFM536-CFN8, pCFM536-CFN8C, pCFM536-CFN11, pCFM536-CFN12, and pCFM536-CFN13 expression vectors.

Firstly, CFN7 (CTP-GGGGGG-IFNα), CFN8 (CTP-GGGG-IFNα), CFN8C (CTP-GGGG-IFNα-C), CFN11 (CTP-KQLRVVNG-IFNα), CFN12 (CTP-GGGGKQLRV-VNGGGG-IFNα) and CFN13 (CTP-AKTKQLRV-VNGGGG-IFNα) PCR products were respectively cloned to pGEM-T vectors, and base sequences thereof were analyzed. Therefore, pGEM-CFN7, pGEM-CFN8, pGEM-CFN8C, pGEM-CFN11, pGEM-CFN12, and pGEM-CFN13 recombinant vectors were obtained which were synthesized without a modification in the desired amino acid sequence. From the recombinant pGEM-CFN7, pGEM-CFN8 and pGEM-CFN8C vectors, inserts were obtained through XbaI and BamHI restriction enzymes, which were included in primers during PCR. Then, the inserts were introduced to pCFM536 vectors to respectively derive expression vectors which were pCFM536-CFN7, pCFM536-CFN8, pCFM536-CFN8C, pCFM536-CFN11, pCFM536-CFN12 and pCFM536-CFN13.

Example 3: Evaluation and Expression of Interferon-Alpha Fusion Protein in E. coli POP2136 competent cells were transformed with pCFM536 vectors, to which CFN7, CFN8, CFN8C, CFN11, CFN12, and CFN13 genes, as prepared in Example 2 were cloned, and then spread on a solid medium having ampicillin added thereto. A colony grown in the solid medium was obtained, inoculated to LB broth medium, and cultured for 18 hours at 30° C. When optical density at 600 nm of wavelength became 0.4 to 0.6, the temperature was raised to 42° C. to induce expression. Culture was continued for additional four hours, and protein expression from the cultured cells was evaluated through SDS-PAGE analysis.

Example 4: Mass Production of Interferon-Alpha Fusion Protein

To prepare a large amount of an IFNα fusion protein, mass culture and purification were performed by using a 5 L fermentation reactor.

1. Mass Culture Using 5 L Fermentor

To prepare a large amount of an IFNα fusion protein by culturing a producing strain, mass culture was performed by using a 5 L fermentor (Biostat B, B. Braun Biotech International). Firstly, a strain, which was proven to express the IFNα fusion protein, was constructed to master cell bank (MCB) and working cell bank (WCB), and stored at −80° C. A day before main culture, the stored WCB was inoculated to 100 ml of 2×YT medium (tryptone 16 g/L, yeast extract 10 g/L, and NaCl g/L) to which ampicillin was added such that a concentration of ampicillin became 50 μg/ml, and cultured for 16 hours at 30° C. For main culture, a culture medium was prepared by adding ampicillin to 3 L of 2×YT medium (tryptone 16 g/L, yeast extract 10 g/L, and NaCl 5 g/L) such that a concentration of ampicillin became 50 μg/ml. As the initial main culture condition, temperature of 30° C., pH 6.8, and vvm 1 were used, and DO was not dropped to 50% or less. An OD value was measured at one hour interval. When the OD value became 10, an additional medium was added, and culture temperature was raised to 42° C. to induce expression. After induction of expression, the OD value was measured at one hour interval, and culture was terminated at the section where the OD value was not increased any more.

2. Isolation of Inclusion Body and Refolding

Cells were collected from cell culture medium above, and collected cells were washed with PBS. Cells were floated in inclusion body washing solution 1 [50 mM Tris (pH 8.0), 1% Triton X-100], disrupted by using a cell disrupter, and then centrifuged to collect an insoluble inclusion body fraction. The insoluble inclusion body fraction was collected by performing the washing process in an order of cell floating, stirring, washing, and centrifuging by sequentially using inclusion body washing solution 1 to 4 [washing solution 1: 50 mM Tris (pH 8.0), 1% Triton X-100, washing solution 2: 50 mM Tris, 1% Triton X-100, 0.1 M NaCl (pH 8.0), washing solution 3: 50 mM Tris, 1% Triton X-100, 0.2 M NaCl (pH 8.0), washing solution 4: 50 mM Tris, 1% Triton X-100, 0.3 M NaCl (pH8.0)].

To obtain a structurally active IFNα fusion protein, isolated inclusion bodies were respectively dissolved in a solubilization buffer which was optimized by each type, and stirred in a respective refolding buffer to perform refolding. The buffers used in solubilization and refolding of each inclusion body of IFN were shown in Table 3 below.

TABLE 3

| Type | Solubilization buffer | Refolding buffer | Refolding condition |
|---|---|---|---|
| IFN | 50 mM Glycine, 8M Urea (pH 11.0) | 50 mM Glycine, 2M Urea (pH 9.5) | Stirring at room temperature for 24 hours |
| CFN7 CFN8 CFN8C CFN11 CFN12 CFN13 | 50 mM tris-HCl, 5 mM EDTA 8M Urea (pH 11.0) | 50 mM tris-HCl, 1 mM EDTA, 2M Urea, 10% Sucrose, 0.1 mM oxidized glutathione, 1 mM reduced glutathione (pH 8.0) | Stirring at 4° C. temperature for 24 hours |

For collection of a protein, cells were floated by adding 0.5 ml of deionized distilled water, and the inclusion body was dissolved by adding a solubilization buffer [6 M Guanidine, 50 mM Tris, 2.5 mM EDTA (pH 9.5)] by 1 ml-basis such that guanidine has the final concentration of 6 M. After completely dissolving the inclusion body by stirring at least four hours, centrifugation (12,000 rpm, 4° C., 30 min) was performed, and supernatant was filtered out by using a 0.2 μm filter.

The completely dissolved inclusion body was refolded by the dilution method. In the refolding buffer (50 mM Tris, 1 mM GSH, 0.2 mM GSSG, 1 mM EDTA, 5% Sucrose, pH 8.0), which has a final guanidine concentration of 1.5 M, the inclusion body was slowly mixed and reacted for 24 hours. After completion of the reaction, acetic acid was added to the sample to adjust pH to 4.0. After additional reaction for at least two hours, the reactant was filtered with 0.2 μm filter. Refolding was evaluated by using RP-HPLC.

3. High-Purity Purification by Using Chromatography

After refolding was performed by the method above, to purify a structurally and normally refolded CTP-X-IFNα-Y protein at high purity, desalting and cation-exchange chromatography were performed.

The completely refolded CTP-X-IFNα-Y protein was dialyzed for 16 hours in a column binding buffer (50 mM Sodium Citrate-Citric acid, and 1 mM EDTA, pH 4.0) to remove 1.5 M of guanidine. A column filled with 10 ml sepharose cation chromatograph resin was installed in FPLC. The column was equilibrated with the column binding buffer (50 mM Sodium Citrate-Citric acid, 1 mM EDTA, pH 4.0), and then sample was loaded on the column. The sample bound to the column was separated by using a concentration gradient buffer (50 mM Sodium Citrate-Citric acid, 1 mM EDTA, and 1 M NaCl, pH 4.0). The separated and purified protein was evaluated by using HPLC analysis. The concentration of the separated sample was measured by using Bradford method and UV spectrometer at 595 nm.

Example 5: Structural Analysis of Interferon-Alpha Fusion Protein

A secondary structure of an IFNα fusion protein, which was constructed by binding a linker as described in the Example above, was analyzed. Analysis of the secondary structure was performed by using interferon α (IFNα), as a control, CFN1 (CTP-IFNα), CFN7 (CTP-GGGGGG-IFNα), CFN8 (CTP-GGGG-IFNα), and Hepsin Cleavage linker-inserted CFN11, CFN12, CFN13. A secondary structure of a protein was analyzed by using a CD spectrophotometer (Jasco-815). A final concentration of a protein to be analyzed was adjusted to 1 mg/ml in 50 mM sodium citrate-citric acid, and 1 mM EDTA (pH4.0). Then, a spectrum was obtained in a range of 190 nm to 250 nm by using quartz cells having a path length of 0.1 cm with 0.2 nm resolution, 1.0 nm bandwidth, and 50 nm/min scan speed at 25° C.

Figure 2:
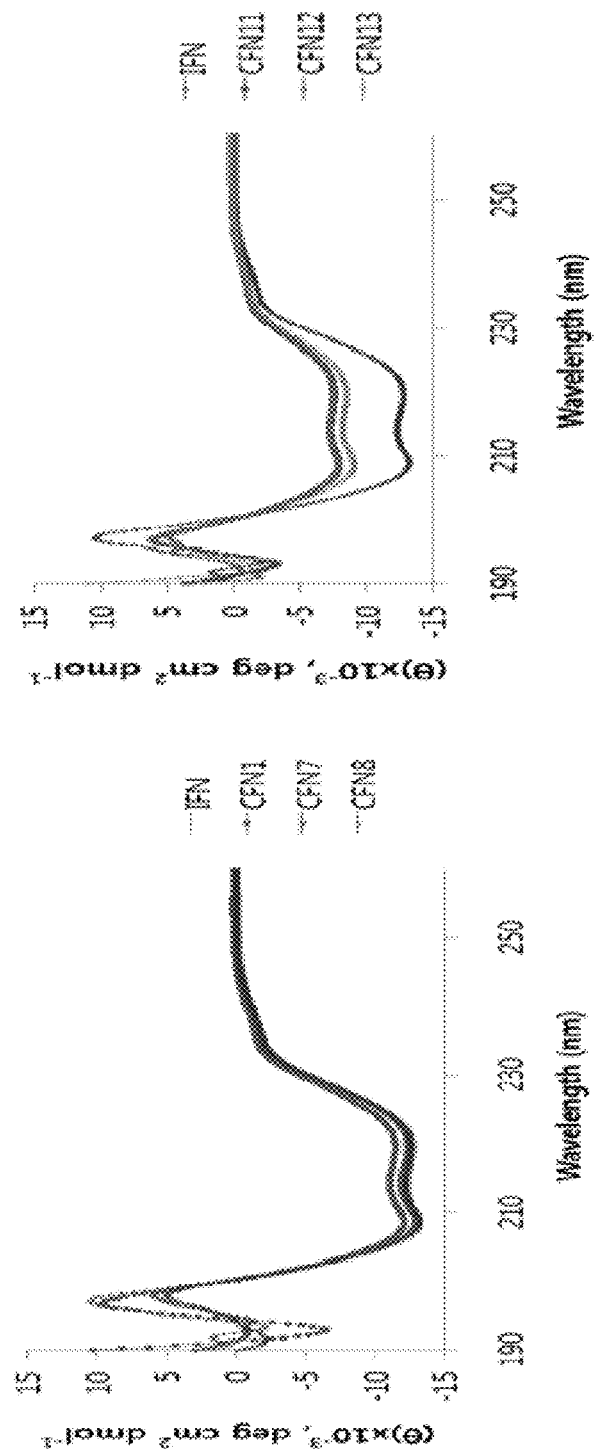
FIG. 2 shows a result obtained by analyzing a secondary structure of the IFNα fusion protein of the present invention prepared by binding a linker through a CD spectrophotometer (Jasco-815).

As a result obtained by analyzing the spectrum shown in FIG. 2, candidate materials, which maintain a secondary structure the most similar to that of interferon-alpha, were CFN7, and CFN8 to which a glycine linker was inserted. For CFN11, CFN12, and CFN13, to which a pepsin cleavage linker was inserted, a modified secondary structure having reduced α-helix was exhibited. Therefore, it was expected that CFN7 and CFN8 IFNα fusion proteins have an activity similar to that of IFNα.

Example 6: Pegylation of Interferon-Alpha Fusion Protein

Figure 3:
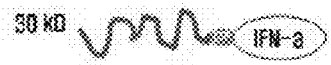
FIG. 3 shows CTP-IFNα-PEG fusion proteins in which PEG is bound to the CTP-INFα fusion protein in various forms.
Figure 3:
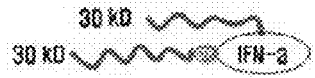
Figure 3:
Figure 3:
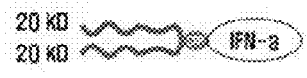
Figure 3:
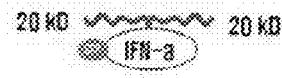
Figure 3:
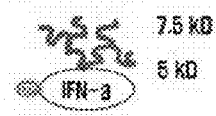
Figure 3:
Figure 3:
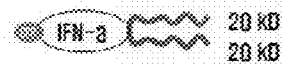

Linear PEG or branched PEG having molecular weight of 30 kDa or 40 kDa was PEGylated at an N-terminal, a C-terminal, or an internal portion. N-terminal PEGylation was a form to which PEG was attached to a head of CTP of an IFNα fusion protein, and internal PEGylation (random PEGylation) was a form in which PEG was randomly attached to a lysine residue within the IFNα fusion protein. Further, C-terminal PEGylation was a form in which linear PEG or branched PEG was attached to the C-terminal of the IFNα fusion protein (see FIG. 3).

For N-terminal PEGylation, a buffer for the IFNα fusion protein CFN8 (CTP-GGGG-IFNα, SEQ ID NO: 33) was replaced by 50 mM sodium phosphate (pH 4.5) buffer. The IFNα fusion protein CFN8 was mixed with aldehyde-PEG at a ratio of 1:10. To this mixture, 1 M NaBH$_3$CN was added as a reducing agent such that the mixture has the final concentration of 20 mM, and the resultant was reacted for two hours at the room temperature. PEGylation degree was evaluated through SDS-PAGE, and a PEGylated protein was finally separated by using cation exchange chromatography and gel filtration chromatography. PEGylation yield was about 40%.

For internal PEGylation, a buffer for the IFNα fusion protein CFN8 (CTP-GGGG-IFNα, SEQ ID NO: 33) was replaced by 50 mM sodium phosphate (pH 7.5) buffer. PEG-NHS ester was mixed at a ratio of 1:10. To this mixture, 1 M NaBH$_3$CN was added as a reducing agent such that the mixture has the final concentration of 20 mM, and the resultant was reacted for two hours at the room temperature. 2 M glycine was added to stop the reaction, and PEGylation degree was evaluated with SDS-PAGE. A PEGylated protein was finally separated through cation exchange chromatography and gel filtration chromatography. PEGylation yield was about 17%.

Among IFNα fusion proteins, C-terminal PEGylation was performed to the CFN8C (CTP-GGGG-IFNα-C, SEQ ID NO: 18) protein having cysteine added to the c-terminal of IFNα. PEG was attached to bind to cysteine produced at the C-terminal of CFN8C (CTP-GGGG-IFNα-C) by using Maleimide-PEG. The protein and PEG were mixed at a ratio of 1:10. The 1 M sodium phosphate (pH 8.0) buffer was added to have the final concentration of 100 mM, and the resultant was reacted for two hours. PEGylation degree was evaluated through SDS-PAGE, and a PEGylated protein was finally separated by using cation exchange chromatography and gel filtration chromatography. PEGylation yield was about 25%.

Respective preparation yields depending on methods of PEGylation were shown in Table 4 below.

Firstly, MDBK cells were diluted to $1.0 \times 10^5$ cells/ml in DMEM medium. Then 200 μl of cells were seed on each well of a 96-well plate, and cultured for 18 hours in a 37° C., 5% CO$_2$ incubator. For a protein, 5000 pg/ml concentration of the interferon-alpha fusion protein, blood diluted to 1/50, a liver sample diluted to 1/10 were prepared, and serially diluted to 1/2. Then, cells were treated with 100 μl of resultant diluents. A reaction was induced for four hours at 37° C. under 5% CO$_2$. Thereafter, VSV was diluted to 0.01 multiplicity of infection (MOI), and added to each cell of the 96-well plate in an amount of 100 μl. After VSV infection, culture was continued for about additional 18 hours to trigger the cytopathic effect. At the end of culture, cells were washed twice with PBS, and fixed by adding 200 μl of 4% formaldehyde to each well. After two times of washing with PBS, 100 μl of 0.05% of crystal violet was added to each well to stain the resultant for 30 minutes. After two times of washing using PBS, drying was performed for 30 minutes. To each well, 100 μl of 80% ethanol was added to dissolve the staining agent, and optical density at 570 nm was measured. The activity was measured by using a well showing 50% of the cytopathic effect, as a standard, compared with an uninfected control.

2. Anti-Viral Activity Measurement Result Depending on Interferon-Alpha Fusion Protein Form By the measurement method above, activities of interferon-alpha fusion proteins, which were CFN 7, CFN 8, CFN 11, CFN 12, and CFN 13, were measured, and the result were shown in Table 5 below.

TABLE 4

| PEGylation method | Functional group (protein) | Functional group (PEG) | Candidate material | CFN8 (mg) | CFN8C (mg) | PEG-CFN8 or CFN8C-PEG (mg) | Yield (%) |
|---|---|---|---|---|---|---|---|
| N-terminal PEGylation | Amine | Aldehyde | 301N-PEG linear type | 26 | | 2.6 | 10 |
| | | | Di-PEG linear type | | | 1.5 | 6 |
| | | | 401N-PEG linear type | 10 | | 2.0 | 20 |
| | | | 202N-PEG branch type | 10 | | 4.0 | 40 |
| Random PEGylation | Amine | NHS-ester | 202K-PEG branch type | 10 | | 1.6 | 17 |
| | | | [2 + 4] K-PEG branch type | | | | |
| C-terminal PEGylation | Thiol | Maleimide | 401C-PEG linear type | | 9 | 2.2 | 25 |
| | | | 202C-PEG branch type | | 9 | 1.6 | 19 |

Example 7: Anti-Viral Activity Measurement of Interferon-Alpha Fusion Protein

1. Method of Measuring Anti-Viral Activity

Anti-viral activities of prepared interferon-alpha fusion proteins were measured by in vitro experiment. The anti-viral activity was measured by degree of abilities of interferon-alpha fusion proteins to alleviate a cytopathic effect caused by vesicular stomatitis virus (VSV) (Korean cell line bank) infection on Madin-Darby bovine kidney (MDBK) (Korean cell line bank) cells.

TABLE 5

| Fusion protein | Relative activities on IFN (%) |
|---|---|
| IFN | 100 |
| CFN7 | 57.6 |
| CFN8 | 90.7 |
| CFN8C | 95.0 |
| CFN11 | 40.8 |

TABLE 5-continued

| Fusion protein | Relative activities on IFN (%) |
|---|---|
| CFN12 | 43.6 |
| CFN13 | 34.2 |

3. Anti-Viral Activity Measurement Result According to PEGylation of Interferon-Alpha Fusion Protein By the measurement method above, measured was an anti-viral activity of the interferon-alpha fusion protein according to differences in the size of PEG and a method for PEGylation.

Measurement of the anti-viral activity was performed on standard IFNα which was an IFNα protein having no CTP and PEG attached thereto; an IFNα fusion protein (CTP-X-IFNα-Y protein) in which CTP was attached to an N-terminal while PEG was not attached; Di-PEG, 202K, [2+4]K, 401C, and 202C which were IFNα fusion proteins in which PEG was attached to an N-terminal or a C-terminal of the CTP-X-IFNα-Y protein in various forms.

The Di-PEG fusion protein was an IFNα fusion protein in which two linear PEGs (30 kDa) were respectively bound to an amine group ($NH_2$) of an N-terminal of the CFN8 protein, and an amine group ($NH_2$) of an internal lysine residue of the protein; the 202K fusion protein was an IFNα fusion protein in which two linear PEGs (20 kDa) were simultaneously bound to the amine group ($NH_2$) of the internal lysine of the CFN8 protein; the [2+4]K fusion protein was an IFNα fusion protein in which two linear PEGs (5 kDa) and four linear PEGs (7.5 kDa) were simultaneously bound to an amine group ($NH_2$) of the internal lysine residue of the CFN8 protein; the 401C fusion protein was an IFNα fusion protein in which one linear PEG (40 kDa) was bound to a sulfhydryl (SH) group of a C-terminal cysteine residue of the CFN8C protein; and the 202C fusion protein was an IFNα fusion protein in which two linear PEGs (20 kDa) were simultaneously bound to sulfhydryl (SH) group of a C-terminal cysteine residue of the CFN8C protein.

As the result described in Table 6 below, comparing with standard IFNα, the anti-viral activity of the IFNα fusion protein to which PEG was not bound was similar to the activity of standard IFNα. On the other hand, although IFNα fusion protein having PEG bound thereto showed various activity values depending on the binding method and types of PEG, all activities thereof were reduced with respect to the standard to which PEG was not attached.

Further, anti-viral activities of 401C, which is the IFNα fusion protein of the present invention, and PEGASYS (Hoffman LaRoche Ltd.), which is a commercially available PEG attached IFNα drug, were measured and compared. PEGASYS is an IFNα fusion protein in which branched PEG (20 kDa) was randomly bound to the IFNα protein. Consequently, as shown in Table 6 below, it has been proven that the 401C fusion protein of the present invention showed the anti-viral activity three times higher than PEGASYS (Hoffman LaRoche Ltd.).

TABLE 6

| | Protein | | Activity rate (%) |
|---|---|---|---|
| Standard | IFNα | | 100.0 |
| PEG unattached | CFN8(CTP-GGGG-IFNα) | CFN8C(CTP-GGGG-IFNα-C) | 95 |
| Various forms of PEG attached protein | Di-PEG | — | 16.7 |
| | 202N | — | 57.2 |
| | 202K | — | 22.1 |
| | [2 + 4]K | — | 17.8 |
| | — | 401C | 32.4 |
| | — | 202C | 39.0 |
| PEGASYS | — | — | 10.8 |

Example 8: Pharmacokinetic Property Measurement of Interferon-Alpha Fusion Protein 1. Pharmacokinetic Data of Mouse Three mice per group were used as a control or an experimental group. A mouse was subcutaneously injected with 30 μg of each interferon-alpha fusion protein sample to a posterior region of neck on time basis (4 h, 8 h, 12 h, 1 d, 2 d, 3 d, 4 d, and 5 d). Samples used in the experiment were as follows: 202K, 202C and 401C fusion proteins as experimental groups; and PEGASYS (Hoffman LaRoche Ltd.) which is a PEG attached IFNα drug as a control. PEGASYS is an IFNα fusion protein in which branched PEG of 20 kDa was randomly bound to the IFNα protein. After the sample was injected, 1 ml of blood was taken from orbit of the mouse at each time point, stayed in ice for one hour, and then centrifuged (13,000 rpm, 4° C., 0.5 h) to collect serum alone. The collected serum was diluted to 1/50 to measure an anti-viral activity. Results of measurement were shown in Table 7 below. As shown in Table 7, it has been proven that the 401C form showed higher activities in blood and liver, and a higher rate of activity in liver to activity in blood than 202K or PEGASYS.

2. Pharmacokinetic Data of Monkey

Two monkeys were used as one group. A monkey was subcutaneously injected with 300 μg/kg of each sample to a posterior region of neck on time basis (4 h, 8 h, 12 h, 1 d, 2 d, 3 d, 4 d, 5 d, and 6 d). As samples, PEGASYS, and the PEG attached IFNα fusion protein, i.e., 401C were used, wherein, 401C was an experimental group and PEGASYS, which is a commercially available IFN-α drug, was used as a control. Prior and post injection, about 2.5 ml of blood was taken from a hind leg vein of the monkey at each time point, stayed in ice for one hour, and centrifuged (13,000 rpm, 4° C., 0.5 h) to collect serum alone. Serum was diluted to 1/50 to measure an anti-viral activity. The result of measurement was shown in FIG. 4.

Figure 4:
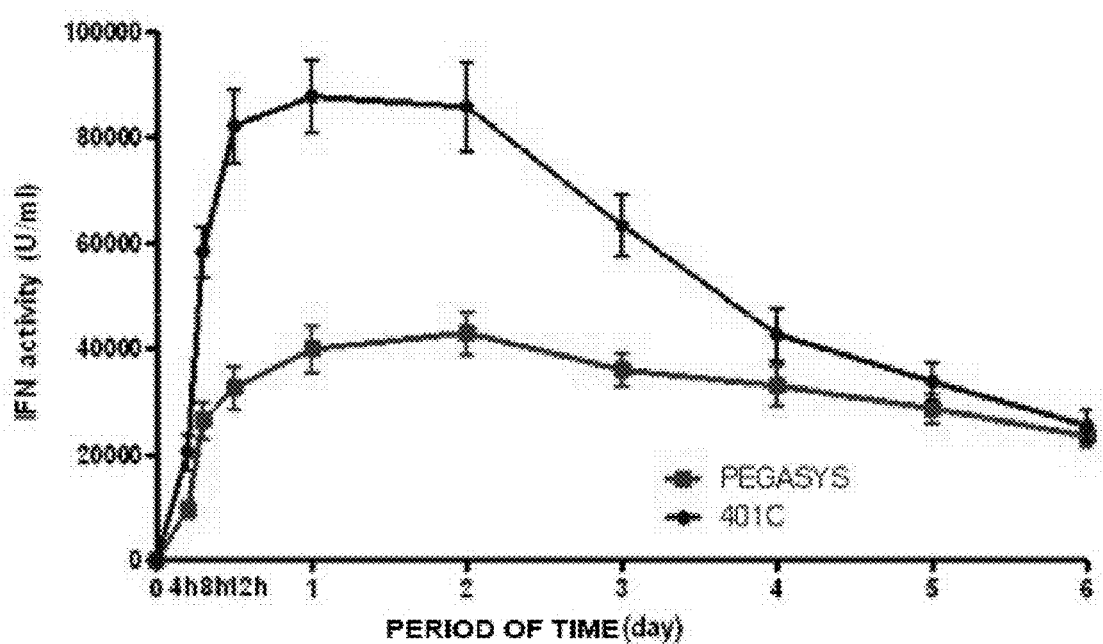
FIG. 4 shows a result obtained by measuring preclinical pharmacokinetics of PEGASYS (Hoffman LaRoche Ltd.) and the IFNα fusion protein of the present invention, i.e., 401C using monkeys. Samples used in the experiment, i.e., PEGASYS and 401C are respectively administered in a dose of 300 μg/kg of body weight. After administering the samples one time, an activity is measured for 6 days. It has been proven that the IFNα fusion protein of the present invention, i.e., 401C has a high IFNα activity, and has an activity which is better than or equivalent to that of PEGASYS, up to 6 days.

In accordance with pharmacokinetic of the interferon-alpha fusion protein of the present invention, i.e., 401C, using a monkey, in an early phase of drug administration, i.e., within three days of administration of the interferon-alpha fusion protein of the present invention 401C, the effect of increasing an initial activity after drug administration similar to that of PEGINTRON (which is a therapeutic agent for hepatitis, Merck & Co., Inc) was showed, and a late phase of drug administration, i.e., within 4 to 7 days after administration, stability similar to that of PEGASYS (which is a therapeutic agent for hepatitis, Hoffman LaRoche Ltd.) was showed (see FIG. 4). These results showed that the interferon-alpha fusion protein, i.e., 401C, prepared in the present invention maintains the high activity up to 7 days while the initial activity is not reduced after drug administration. Such persistency was proven that a type and a position of polyethylene glycol, and a linker, and a method to form the fusion protein according to one example of the present invention were optimized.

Example 9: Measurement of Ability of Interferon Alpha Fusion Protein to Migrate to Liver Three mice per group were subcutaneously injected with 30 μg of each sample to a posterior region of neck of the mouse on time basis (4 h, 8 h, 12 h, 1 d, 2 d, 3 d, 4 d, and 5 d). Samples used in the experiment were as follows: 202K, 202C and 401C fusion proteins as experimental group; and PEGASYS (Hoffman LaRoche Ltd.) which is a PEG attached IFNα drug as a control. After injection, liver perfusion was performed at each time point by infusing cold-stored PBS into a blood vessel of liver after incising abdomen of the mouse. After removing blood from liver, whole liver was dissected, and placed into 10% sucrose buffer. Then liver was washed with PBS two times. Liver was placed to the PBS buffer containing a protease inhibitor, and then disrupted by a disrupter. 400 μl of the 10×RIPA buffer was added and mixed to become the 1×RIPA buffer. About 1.2 ml per sample was aliquoted to three 1.5 ml tubes, and stored for 12 hours at 4° C. After centrifugation (13,000 rpm, 4□, 0.5 h), only 700 μl of supernatant was collected from each tube, and thus about 2 ml for each sample was collected. 1 ml of the sample was purified through FPLC (using Hi-trap desalting column, fixed flow of 3). To measure an amount of a collected protein fraction, area under concentration (AUC) was measured to calculate dilution fold. [ELISA measured value (ng/ml)×2×2×total disrupted volume (ml)]/[weight of liver (g)×(amount of protein obtained by FPLC purification)/(total amount of FPLC purified protein)]=ng/g of liver. Using liver extracts at each time point, the activity of interferon-α was measured, and thus abilities of the PEG-attached interferon-α fusion protein and the commercial drug, PEGASYS, to migrate into liver were compared and evaluated.

Figure 5A:
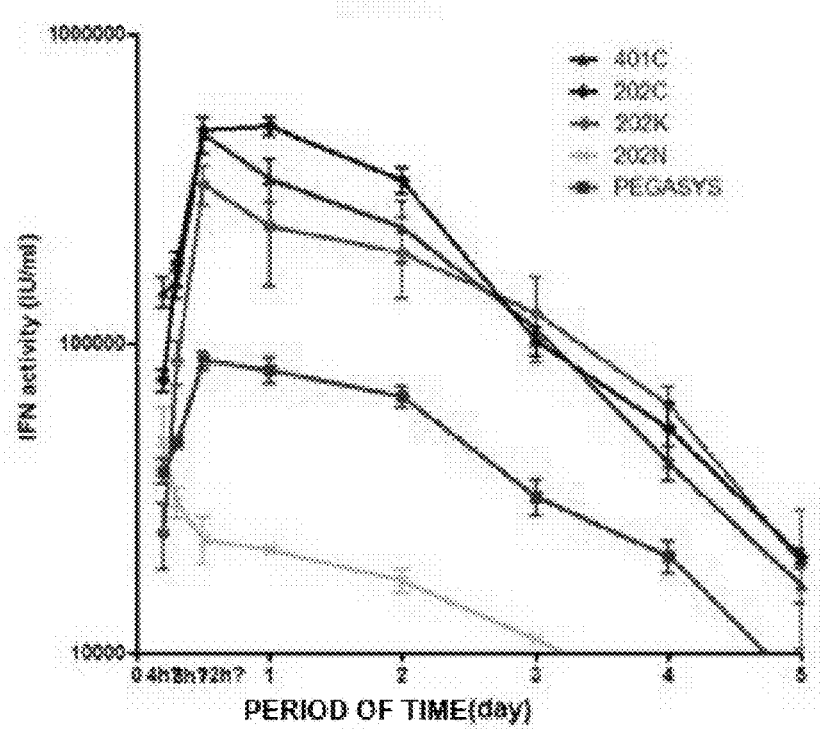
FIGS. 5a and 5b show a result obtained by comparing abilities of the fusion protein of the present invention and a control drug to migrate into cells. After administering, to a mouse, the interferon-alpha fusion protein of the present invention and the control drug PEGASYS (Hoffman LaRoche Ltd.), anti-viral activities depending on time are respectively measured in blood (FIG. 5a) and liver (FIG. 5b).
Figure 5B:
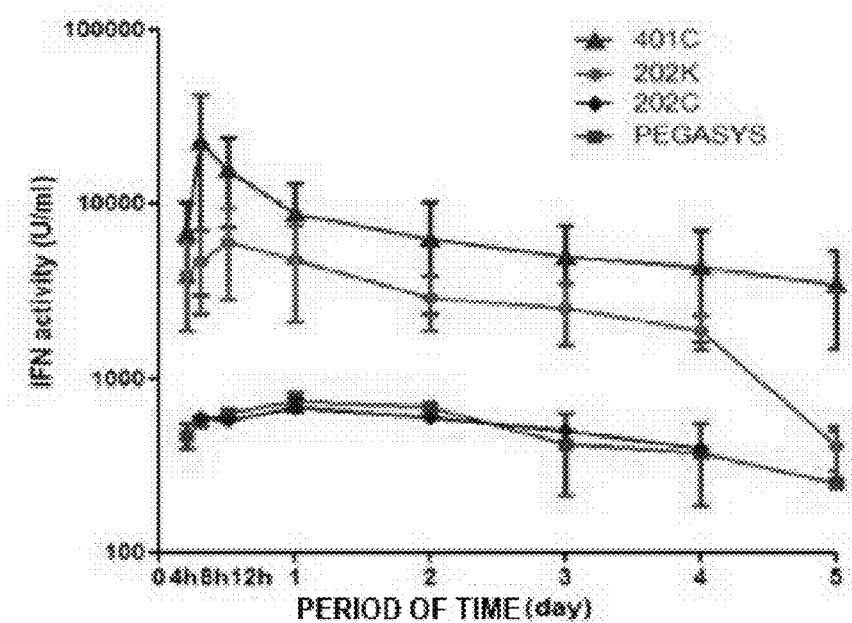

As shown in results of FIGS. 5a and 5b, according to the experiment result of measuring an ability to migrate into liver by using a mouse, the ability to migrate into liver of the interferon-alpha fusion protein of the present invention 401C was about 13 times higher and the ability to migrate into liver of the interferon-alpha fusion protein of the present invention 202K was about 6 times higher than PEGASYS. Considering that PEGASYS has a high ability to migrate into liver due to the intrinsic PEG, it has been proven that the ability of the interferon-alpha fusion protein of the present invention to migrate into liver is significantly high. In addition, for 202N, it has been found that almost no ability to migrate into liver was shown. Because of a form of 202N, it is considered that the ability of CTP to migrate into liver is hindered since PEG is PEGylated at a C-terminal of the CTP.

Table 7 below shows results comparing the activity values of 401C and 202K, which are pharmacokinetically best experimental groups, with the activity value of PEGASYS which is a control. Consequently, 401C showed the most excellent pharmacokinetic activity in liver and blood when compared with the experimental group, as well as, the control.

TABLE 7

| Fusion protein | Activity in blood (AUC) (IU · d/ml) | | Activity in liver (AUC) (IU · d/g liver) | | Activity in liver/ Activity in blood (%) |
|---|---|---|---|---|---|
| | Measured value | Fold comparing to PEGASYS | Measured value | Fold comparing to PEGASYS | |
| 401C | 850,333 | 3.7 | 32,986 | 13 | 3.87 |
| 202C | 1,084,000 | 4.8 | 2,078 | 0.84 | 0.19 |
| 202K | 704,042 | 3.1 | 14,150 | 5.7 | 2.00 |
| 202N | 62,767 | 0.3 | 0 | 0 | 0 |
| PEGASYS | 225,267 | 1.0 | 2,463 | 1.0 | 1.09 |

To sum up, the present invention relates to an interferon alpha fusion protein having improved retention property and ability to migrate to liver. The present invention was completed by selecting a linker which does not induce a structural modification based on the structure of the interferon-alpha fusion protein depending on types and sizes of the linker to link the fusion protein, and demonstrating that the activity of the interferon alpha protein, the interferon alpha protein's ability to migrate to liver, and retention property of the interferon alpha protein are improved through the in vivo and in vitro properties of the fusion protein. Further, the fusion protein according to one example of the present invention has the improved activity and half-life comparing with the convention fusion protein. Also, preparation and quality control of the fusion protein according to one example of the present invention is easy. Therefore, the fusion protein according to one example of the present invention may be usefully applied as a composition for treating liver diseases.

Hitherto, specific features of the present invention are described in detail. However, it would be apparent to a person skilled in the art that the specific description is preferable embodiment only, and the scope of the invention is not limited thereto. Therefore, substantial scope of the present invention would be defined by accompanying claims and equivalents thereof.

The invention claimed is:

1. A fusion protein comprising interferon-alpha (IFN-α) protein fused to a cytoplasmic transduction peptide (CTP) and polyethylene glycol (PEG), further comprising linkers, wherein the fusion protein is of the structure: CTP-X-IFNα-Y-PEG, wherein the fusion protein comprises an amino acid sequence selected from the group consisting of SEQ ID NOs:15 to 20 and further comprises polyethylene glycol (PEG) bound thereto.

2. The fusion protein of claim 1, wherein, the polyethylene glycol (PEG) is linear PEG.

3. The fusion protein of claim 1, wherein, the molecular weight of the PEG is 20 to 60 kDa.

4. A nucleic acid molecule coding a peptide moiety of the formula: "CTP-X-IFNα-Y" within the fusion protein of claim 1.

5. A vector comprising the nucleic acid molecule of claim 4.

6. A transformant transformed with the vector of claim 5.

7. A pharmaceutical composition comprising: (a) a pharmaceutically effective amount of the fusion protein of claim 1; and (b) a pharmaceutically acceptable carrier.

8. A method of treating liver disease in a patient with liver disease, the method comprising administering a pharmaceutical composition of claim 7 to the patient with liver disease.

9. The method of claim 8, wherein the liver disease is a hepatoma cancer or hepatitis.

10. The method of claim 8, wherein the hepatitis is hepatitis type C caused by Hepatitis C virus (HCV).

* * * * *

SEQUENCE LISTING

<160> NUMBER OF SEQ ID NOS: 38

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct

<400> SEQUENCE: 1

Tyr Gly Arg Arg Ala Arg Arg Arg Arg Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Construct

<400> SEQUENCE: 2

Tyr Gly Arg Arg Ala Arg Arg Arg Ala Arg Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Tyr Gly Arg Arg Ala Arg Arg Ala Ala Arg Arg
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Tyr Lys Arg Lys Ala Arg Arg Ala Ala Arg Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Tyr Ala Arg Lys Ala Arg Arg Ala Ala Arg Arg
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Construct

<400> SEQUENCE: 6

Tyr Lys Arg Ala Ala Arg Arg Ala Ala Arg Arg
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

Tyr Glu Arg Glu Ala Arg Arg Ala Ala Arg Arg
1               5                   10

```
<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Tyr Ala Arg Glu Ala Arg Arg Ala Ala Arg Arg
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Construct

<400> SEQUENCE: 9

Tyr Gly Arg Ala Ala Arg Arg Ala Ala Arg Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Tyr Arg Arg Ala Ala Arg Arg Ala Ala Arg Ala
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Tyr Pro Arg Ala Ala Arg Arg Ala Ala Arg Arg
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Pro Ala Arg Ala Ala Arg Arg Ala Ala Arg Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic Construct

<400> SEQUENCE: 13

Tyr Gly Arg Arg Arg Arg Arg Arg Arg Arg Arg
1               5                   10

<210> SEQ ID NO 14
```

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 14

Tyr Arg Arg Arg Arg Arg Arg Arg Arg Arg Arg
1               5                   10

<210> SEQ ID NO 15
<211> LENGTH: 180
<212> TYPE: PRT
<213> ORGANISM: Artificial Sequence
<220> FEATURE:
<223> OTHER INFORMATION: Synthetic Construct

<400> SEQUENCE: 15

Met Tyr Gly Arg Arg Ala Arg Arg Arg Arg Gly Gly Cys Asp
1               5                   10                  15

Leu Pro Gln Thr His Ser Leu Gly Ser Arg Arg Thr Leu Met Leu Leu
                20                  25                  30

Ala Gln Met Arg Arg Ile Ser Leu Phe Ser Cys Leu Lys Asp Arg His
            35                  40                  45

Asp Phe Gly Phe Pro Gln Glu Glu Phe Gly Asn Gln Phe Gln Lys Ala
        50                  55                  60

Glu Thr Ile Pro Val Leu His Glu Met Ile Gln Ile Phe Asn Leu
65                  70                  75                  80

Phe Ser Thr Lys Asp Ser Ser Ala Ala Trp Asp Glu Thr Leu Leu Asp
                85                  90                  95

Lys Phe Tyr Thr Glu Leu Tyr Gln Gln Leu Asn Asp Leu Glu Ala Cys
            100                 105                 110

Val Ile Gln Gly Val Gly Val Thr Glu Thr Pro Leu Met Lys Glu Asp
        115                 120                 125

Ser Ile Leu Ala Val Arg Lys Tyr Phe Gln Arg Ile Thr Leu Tyr Leu
    130                 135                 140

Lys Glu Lys Lys Tyr Ser Pro Cys Ala Trp Glu Val Val Arg Ala Glu
145                 150                 155                 160

Ile Met Arg Ser Phe Ser Leu Ser Thr Asn Leu Gln Glu Ser Leu Arg
                165                 170                 175

Ser Lys Glu Cys
            180

<210> SEQ ID NO 16
<211> LENGTH: 183
<212> TYPE: PRT
<213> ORGANISM: Artificial Sequence
<220> FEATURE:
<223> OTHER INFORMATION: Synthetic Construct

<400> SEQUENCE: 16

Met Tyr Gly Arg Arg Ala Arg Arg Arg Arg Gly Gly Gly
1               5                   10                  15

Cys Asp Leu Pro Gln Thr His Ser Leu Gly Ser Arg Arg Thr Leu Met
                20                  25                  30

Leu Leu Ala Gln Met Arg Arg Ile Ser Leu Phe Ser Cys Leu Lys Asp
            35                  40                  45

Arg His Asp Phe Gly Phe Pro Gln Glu Glu Phe Gly Asn Gln Phe Gln
        50                  55                  60
```

```
Lys Ala Glu Thr Ile Pro Val Leu His Glu Met Ile Gln Gln Ile Phe
 65                  70                  75                  80

Asn Leu Phe Ser Thr Lys Asp Ser Ser Ala Ala Trp Asp Glu Thr Leu
                 85                  90                  95

Leu Asp Lys Phe Tyr Thr Glu Leu Tyr Gln Gln Leu Asn Asp Leu Glu
            100                 105                 110

Ala Cys Val Ile Gln Gly Val Gly Val Thr Glu Thr Pro Leu Met Lys
        115                 120                 125

Glu Asp Ser Ile Leu Ala Val Arg Lys Tyr Phe Gln Arg Ile Thr Leu
    130                 135                 140

Tyr Leu Lys Glu Lys Lys Tyr Ser Pro Cys Ala Trp Glu Val Val Arg
145                 150                 155                 160

Ala Glu Ile Met Arg Ser Phe Ser Leu Ser Thr Asn Leu Gln Glu Ser
                165                 170                 175

Leu Arg Ser Lys Glu Gly Cys
            180
```

<210> SEQ ID NO 17
<211> LENGTH: 181
<212> TYPE: PRT
<213> ORGANISM: Artificial Sequence
<220> FEATURE:
<223> OTHER INFORMATION: Synthetic Construct

<400> SEQUENCE: 17

```
Met Tyr Gly Arg Arg Ala Arg Arg Arg Arg Arg Gly Gly Cys Asp
1               5                   10                  15

Leu Pro Gln Thr His Ser Leu Gly Ser Arg Arg Thr Leu Met Leu Leu
                 20                  25                  30

Ala Gln Met Arg Arg Ile Ser Leu Phe Ser Cys Leu Lys Asp Arg His
            35                  40                  45

Asp Phe Gly Phe Pro Gln Glu Glu Phe Gly Asn Gln Phe Gln Lys Ala
        50                  55                  60

Glu Thr Ile Pro Val Leu His Glu Met Ile Gln Gln Ile Phe Asn Leu
 65                  70                  75                  80

Phe Ser Thr Lys Asp Ser Ser Ala Ala Trp Asp Glu Thr Leu Leu Asp
                 85                  90                  95

Lys Phe Tyr Thr Glu Leu Tyr Gln Gln Leu Asn Asp Leu Glu Ala Cys
            100                 105                 110

Val Ile Gln Gly Val Gly Val Thr Glu Thr Pro Leu Met Lys Glu Asp
        115                 120                 125

Ser Ile Leu Ala Val Arg Lys Tyr Phe Gln Arg Ile Thr Leu Tyr Leu
    130                 135                 140

Lys Glu Lys Lys Tyr Ser Pro Cys Ala Trp Glu Val Val Arg Ala Glu
145                 150                 155                 160

Ile Met Arg Ser Phe Ser Leu Ser Thr Asn Leu Gln Glu Ser Leu Arg
                165                 170                 175

Ser Lys Glu Cys Cys
            180
```

<210> SEQ ID NO 18
<211> LENGTH: 182
<212> TYPE: PRT
<213> ORGANISM: Artificial Sequence
<220> FEATURE:
<223> OTHER INFORMATION: Synthetic Construct

<400> SEQUENCE: 18

```
Met Tyr Gly Arg Arg Ala Arg Arg Arg Arg Gly Gly Gly Gly
1               5                   10                  15

Cys Asp Leu Pro Gln Thr His Ser Leu Gly Ser Arg Arg Thr Leu Met
            20                  25                  30

Leu Leu Ala Gln Met Arg Arg Ile Ser Leu Phe Ser Cys Leu Lys Asp
            35                  40                  45

Arg His Asp Phe Gly Phe Pro Gln Glu Glu Phe Gly Asn Gln Phe Gln
            50                  55                  60

Lys Ala Glu Thr Ile Pro Val Leu His Glu Met Ile Gln Gln Ile Phe
65                  70                  75                  80

Asn Leu Phe Ser Thr Lys Asp Ser Ser Ala Ala Trp Asp Glu Thr Leu
                85                  90                  95

Leu Asp Lys Phe Tyr Thr Glu Leu Tyr Gln Gln Leu Asn Asp Leu Glu
                100                 105                 110

Ala Cys Val Ile Gln Gly Val Gly Val Thr Glu Thr Pro Leu Met Lys
            115                 120                 125

Glu Asp Ser Ile Leu Ala Val Arg Lys Tyr Phe Gln Arg Ile Thr Leu
130                 135                 140

Tyr Leu Lys Glu Lys Lys Tyr Ser Pro Cys Ala Trp Glu Val Val Arg
145                 150                 155                 160

Ala Glu Ile Met Arg Ser Phe Ser Leu Ser Thr Asn Leu Gln Glu Ser
                165                 170                 175

Leu Arg Ser Lys Glu Cys
            180

<210> SEQ ID NO 19
<211> LENGTH: 184
<212> TYPE: PRT
<213> ORGANISM: Artificial Sequence
<220> FEATURE:
<223> OTHER INFORMATION: Synthetic Construct

<400> SEQUENCE: 19

Met Tyr Gly Arg Arg Ala Arg Arg Arg Arg Gly Gly Gly Gly
1               5                   10                  15

Gly Gly Cys Asp Leu Pro Gln Thr His Ser Leu Gly Ser Arg Arg Thr
            20                  25                  30

Leu Met Leu Leu Ala Gln Met Arg Arg Ile Ser Leu Phe Ser Cys Leu
            35                  40                  45

Lys Asp Arg His Asp Phe Gly Phe Pro Gln Glu Glu Phe Gly Asn Gln
            50                  55                  60

Phe Gln Lys Ala Glu Thr Ile Pro Val Leu His Glu Met Ile Gln Gln
65                  70                  75                  80

Ile Phe Asn Leu Phe Ser Thr Lys Asp Ser Ser Ala Ala Trp Asp Glu
                85                  90                  95

Thr Leu Leu Asp Lys Phe Tyr Thr Glu Leu Tyr Gln Gln Leu Asn Asp
                100                 105                 110

Leu Glu Ala Cys Val Ile Gln Gly Val Gly Val Thr Glu Thr Pro Leu
            115                 120                 125

Met Lys Glu Asp Ser Ile Leu Ala Val Arg Lys Tyr Phe Gln Arg Ile
            130                 135                 140

Thr Leu Tyr Leu Lys Glu Lys Lys Tyr Ser Pro Cys Ala Trp Glu Val
145                 150                 155                 160

Val Arg Ala Glu Ile Met Arg Ser Phe Ser Leu Ser Thr Asn Leu Gln
                165                 170                 175
```

```
Glu Ser Leu Arg Ser Lys Glu Cys
            180

<210> SEQ ID NO 20
<211> LENGTH: 185
<212> TYPE: PRT
<213> ORGANISM: Artificial Sequence
<220> FEATURE:
<223> OTHER INFORMATION: Synthetic Construct

<400> SEQUENCE: 20

Met Tyr Gly Arg Arg Ala Arg Arg Arg Arg Gly Gly Gly Gly
1               5                   10                  15

Gly Gly Cys Asp Leu Pro Gln Thr His Ser Leu Gly Ser Arg Arg Thr
            20                  25                  30

Leu Met Leu Leu Ala Gln Met Arg Arg Ile Ser Leu Phe Ser Cys Leu
        35                  40                  45

Lys Asp Arg His Asp Phe Gly Phe Pro Gln Glu Glu Phe Gly Asn Gln
    50                  55                  60

Phe Gln Lys Ala Glu Thr Ile Pro Val Leu His Glu Met Ile Gln Gln
65                  70                  75                  80

Ile Phe Asn Leu Phe Ser Thr Lys Asp Ser Ser Ala Ala Trp Asp Glu
                85                  90                  95

Thr Leu Leu Asp Lys Phe Tyr Thr Glu Leu Tyr Gln Gln Leu Asn Asp
            100                 105                 110

Leu Glu Ala Cys Val Ile Gln Gly Val Gly Val Thr Glu Thr Pro Leu
        115                 120                 125

Met Lys Glu Asp Ser Ile Leu Ala Val Arg Lys Tyr Phe Gln Arg Ile
    130                 135                 140

Thr Leu Tyr Leu Lys Glu Lys Tyr Ser Pro Cys Ala Trp Glu Val
145                 150                 155                 160

Val Arg Ala Glu Ile Met Arg Ser Phe Ser Leu Ser Thr Asn Leu Gln
                165                 170                 175

Glu Ser Leu Arg Ser Lys Glu Gly Cys
            180                 185

<210> SEQ ID NO 21
<211> LENGTH: 165
<212> TYPE: PRT
<213> ORGANISM: Artificial Sequence
<220> FEATURE:
<223> OTHER INFORMATION: Synthetic Construct

<400> SEQUENCE: 21

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
```

```
                   100                 105                 110
Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 22
<211> LENGTH: 546
<212> TYPE: DNA
<213> ORGANISM: Artificial Sequence
<220> FEATURE:
<223> OTHER INFORMATION: Synthetic Construct

<400> SEQUENCE: 22
atgtatggtc gtcgtgcacg tcgtcgtcgt cgtcgtggtg gtggtggttg cgatctgccg      60
cagacccata gcctgggcag ccgtcgtacc ctgatgctgc tggcgcagat gcgtcgtatc     120
agcctgttta gctgcctgaa agatcgtcat gatttttggct ttccgcagga agaatttggc    180
aaccagtttc agaaagcgga aaccatcccg gtgctgcatg aaatgatcca gcagatcttt     240
aacctgttta gcaccaaaga tagcagcgcg cgtgggatg aaaccctgct ggataaattt      300
tataccgaac tgtatcagca gctgaacgat ctggaagcgt gcgtgatcca gggcgtgggc    360
gtgaccgaaa ccccgctgat gaagaagat agcatcctgg cggtgcgtaa atattttcag     420
cgtatcaccc tgtatctgaa ggaaaaaaaa tatagcccgt gcgcgtggga agtggtgcgt   480
gcggaaatca tgcgtagctt tagcctgagc accaacctgc aagaaagcct gcgtagcaaa   540
gaatgc                                                               546

<210> SEQ ID NO 23
<211> LENGTH: 53
<212> TYPE: DNA
<213> ORGANISM: Artificial Sequence
<220> FEATURE:
<223> OTHER INFORMATION: Synthetic Construct

<400> SEQUENCE: 23
taatctagaa aaaccaagg aggtaataac atatgtatgg tcgtcgtgca cgt           53

<210> SEQ ID NO 24
<211> LENGTH: 39
<212> TYPE: DNA
<213> ORGANISM: Artificial Sequence
<220> FEATURE:
<223> OTHER INFORMATION: Synthetic Construct

<400> SEQUENCE: 24
caaggatccc tcgagctatt attctttgct acgcaggct                           39

<210> SEQ ID NO 25
<211> LENGTH: 69
<212> TYPE: DNA
<213> ORGANISM: Artificial Sequence
<220> FEATURE:
<223> OTHER INFORMATION: Synthetic Construct

<400> SEQUENCE: 25
tatggtcgtc gtgcacgtcg tcgtcgtcgt cgtggtggtg gtggtggtgg ttgcgatctg    60
``` ccgcagacc                                                                    69

<210> SEQ ID NO 26
<211> LENGTH: 63
<212> TYPE: DNA
<213> ORGANISM: Artificial Sequence
<220> FEATURE:
<223> OTHER INFORMATION: Synthetic Construct

<400> SEQUENCE: 26
tatggtcgtc gtgcacgtcg tcgtcgtcgt cgtggtggtg gtggttgcga tctgccgcag      60
acc                                                                    63

<210> SEQ ID NO 27
<211> LENGTH: 75
<212> TYPE: DNA
<213> ORGANISM: Artificial Sequence
<220> FEATURE:
<223> OTHER INFORMATION: Synthetic Construct

<400> SEQUENCE: 27
tatggtcgtc gtgcacgtcg tcgtcgtcgt cgtaaacagc tgcgtgtggt gaacggttgc      60
gatctgccgc agacc                                                       75

<210> SEQ ID NO 28
<211> LENGTH: 96
<212> TYPE: DNA
<213> ORGANISM: Artificial Sequence
<220> FEATURE:
<223> OTHER INFORMATION: Synthetic Construct

<400> SEQUENCE: 28
tatggtcgtc gtgcacgtcg tcgtcgtcgt cgtggtggtg gtggtaaaca gctgcgtgtg      60
gtgaacggtg gtggtggttg cgatctgccg cagacc                                96

<210> SEQ ID NO 29
<211> LENGTH: 93
<212> TYPE: DNA
<213> ORGANISM: Artificial Sequence
<220> FEATURE:
<223> OTHER INFORMATION: Synthetic Construct

<400> SEQUENCE: 29
tatggtcgtc gtgcacgtcg tcgtcgtcgt cgtgcaaaaa ccaaacagct gcgtgtggtg      60
aacggtggtg gtggttgcga tctgccgcag acc                                   93

<210> SEQ ID NO 30
<211> LENGTH: 40
<212> TYPE: DNA
<213> ORGANISM: Artificial Sequence
<220> FEATURE:
<223> OTHER INFORMATION: Synthetic Construct

<400> SEQUENCE: 30
ctagtctaga aaaaccaag gaggtaataa catatgtatg                              40

<210> SEQ ID NO 31
<211> LENGTH: 55
<212> TYPE: DNA
<213> ORGANISM: Artificial Sequence
<220> FEATURE:
<223> OTHER INFORMATION: Synthetic Construct

```
<400> SEQUENCE: 31
cgcggatccc tattagcaac caccaccacc ttctttgcta cgcaggcttt cttgc        55

<210> SEQ ID NO 32
<211> LENGTH: 183
<212> TYPE: PRT
<213> ORGANISM: Artificial Sequence
<220> FEATURE:
<223> OTHER INFORMATION: Synthetic Construct

<400> SEQUENCE: 32

Met Tyr Gly Arg Arg Ala Arg Arg Arg Arg Gly Gly Gly Gly
1               5                   10                  15

Gly Gly Cys Asp Leu Pro Gln Thr His Ser Leu Gly Ser Arg Arg Thr
            20                  25                  30

Leu Met Leu Leu Ala Gln Met Arg Arg Ile Ser Leu Phe Ser Cys Leu
        35                  40                  45

Lys Asp Arg His Asp Phe Gly Phe Pro Gln Glu Glu Phe Gly Asn Gln
50                  55                  60

Phe Gln Lys Ala Glu Thr Ile Pro Val Leu His Glu Met Ile Gln Gln
65                  70                  75                  80

Ile Phe Asn Leu Phe Ser Thr Lys Asp Ser Ser Ala Ala Trp Asp Glu
                85                  90                  95

Thr Leu Leu Asp Lys Phe Tyr Thr Glu Leu Tyr Gln Gln Leu Asn Asp
            100                 105                 110

Leu Glu Ala Cys Val Ile Gln Gly Val Gly Val Thr Glu Thr Pro Leu
        115                 120                 125

Met Lys Glu Asp Ser Ile Leu Ala Val Arg Lys Tyr Phe Gln Arg Ile
130                 135                 140

Thr Leu Tyr Leu Lys Glu Lys Tyr Ser Pro Cys Ala Trp Glu Val
145                 150                 155                 160

Val Arg Ala Glu Ile Met Arg Ser Phe Ser Leu Ser Thr Asn Leu Gln
                165                 170                 175

Glu Ser Leu Arg Ser Lys Glu
            180

<210> SEQ ID NO 33
<211> LENGTH: 181
<212> TYPE: PRT
<213> ORGANISM: Artificial Sequence
<220> FEATURE:
<223> OTHER INFORMATION: Synthetic Construct

<400> SEQUENCE: 33

Met Tyr Gly Arg Arg Ala Arg Arg Arg Arg Gly Gly Gly Gly
1               5                   10                  15

Cys Asp Leu Pro Gln Thr His Ser Leu Gly Ser Arg Arg Thr Leu Met
            20                  25                  30

Leu Leu Ala Gln Met Arg Arg Ile Ser Leu Phe Ser Cys Leu Lys Asp
        35                  40                  45

Arg His Asp Phe Gly Phe Pro Gln Glu Glu Phe Gly Asn Gln Phe Gln
    50                  55                  60

Lys Ala Glu Thr Ile Pro Val Leu His Glu Met Ile Gln Gln Ile Phe
65                  70                  75                  80

Asn Leu Phe Ser Thr Lys Asp Ser Ser Ala Ala Trp Asp Glu Thr Leu
                85                  90                  95

Leu Asp Lys Phe Tyr Thr Glu Leu Tyr Gln Gln Leu Asn Asp Leu Glu
```

```
            100                 105                 110
Ala Cys Val Ile Gln Gly Val Gly Val Thr Glu Thr Pro Leu Met Lys
        115                 120                 125

Glu Asp Ser Ile Leu Ala Val Arg Lys Tyr Phe Gln Arg Ile Thr Leu
    130                 135                 140

Tyr Leu Lys Glu Lys Lys Tyr Ser Pro Cys Ala Trp Glu Val Val Arg
145                 150                 155                 160

Ala Glu Ile Met Arg Ser Phe Ser Leu Ser Thr Asn Leu Gln Glu Ser
                165                 170                 175

Leu Arg Ser Lys Glu
            180

<210> SEQ ID NO 34
<211> LENGTH: 185
<212> TYPE: PRT
<213> ORGANISM: Artificial Sequence
<220> FEATURE:
<223> OTHER INFORMATION: Synthetic Construct

<400> SEQUENCE: 34

Met Tyr Gly Arg Arg Ala Arg Arg Arg Arg Arg Lys Gln Leu Arg
1               5                   10                  15

Val Val Asn Gly Cys Asp Leu Pro Gln Thr His Ser Leu Gly Ser Arg
                20                  25                  30

Arg Thr Leu Met Leu Leu Ala Gln Met Arg Arg Ile Ser Leu Phe Ser
            35                  40                  45

Cys Leu Lys Asp Arg His Asp Phe Gly Phe Pro Gln Glu Glu Phe Gly
        50                  55                  60

Asn Gln Phe Gln Lys Ala Glu Thr Ile Pro Val Leu His Glu Met Ile
65                  70                  75                  80

Gln Gln Ile Phe Asn Leu Phe Ser Thr Lys Asp Ser Ser Ala Ala Trp
                85                  90                  95

Asp Glu Thr Leu Leu Asp Lys Phe Tyr Thr Glu Leu Tyr Gln Gln Leu
            100                 105                 110

Asn Asp Leu Glu Ala Cys Val Ile Gln Gly Val Gly Val Thr Glu Thr
        115                 120                 125

Pro Leu Met Lys Glu Asp Ser Ile Leu Ala Val Arg Lys Tyr Phe Gln
    130                 135                 140

Arg Ile Thr Leu Tyr Leu Lys Glu Lys Lys Tyr Ser Pro Cys Ala Trp
145                 150                 155                 160

Glu Val Val Arg Ala Glu Ile Met Arg Ser Phe Ser Leu Ser Thr Asn
                165                 170                 175

Leu Gln Glu Ser Leu Arg Ser Lys Glu
            180                 185

<210> SEQ ID NO 35
<211> LENGTH: 192
<212> TYPE: PRT
<213> ORGANISM: Artificial Sequence
<220> FEATURE:
<223> OTHER INFORMATION: Synthetic Construct

<400> SEQUENCE: 35

Met Tyr Gly Arg Arg Ala Arg Arg Arg Arg Arg Gly Gly Gly
1               5                   10                  15

Lys Gln Leu Arg Val Val Asn Gly Gly Gly Gly Cys Asp Leu Pro Gln
                20                  25                  30
```

-continued

```
Thr His Ser Leu Gly Ser Arg Arg Thr Leu Met Leu Ala Gln Met
         35                  40                  45
Arg Arg Ile Ser Leu Phe Ser Cys Leu Lys Asp Arg His Asp Phe Gly
 50                  55                  60
Phe Pro Gln Glu Glu Phe Gly Asn Gln Phe Gln Lys Ala Glu Thr Ile
 65                  70                  75                  80
Pro Val Leu His Glu Met Ile Gln Gln Ile Phe Asn Leu Phe Ser Thr
                 85                  90                  95
Lys Asp Ser Ser Ala Ala Trp Asp Glu Thr Leu Leu Asp Lys Phe Tyr
            100                 105                 110
Thr Glu Leu Tyr Gln Gln Leu Asn Asp Leu Glu Ala Cys Val Ile Gln
        115                 120                 125
Gly Val Gly Val Thr Glu Thr Pro Leu Met Lys Glu Asp Ser Ile Leu
130                 135                 140
Ala Val Arg Lys Tyr Phe Gln Arg Ile Thr Leu Tyr Leu Lys Glu Lys
145                 150                 155                 160
Lys Tyr Ser Pro Cys Ala Trp Glu Val Val Arg Ala Glu Ile Met Arg
                165                 170                 175
Ser Phe Ser Leu Ser Thr Asn Leu Gln Glu Ser Leu Arg Ser Lys Glu
            180                 185                 190
```

<210> SEQ ID NO 36
<211> LENGTH: 191
<212> TYPE: PRT
<213> ORGANISM: Artificial Sequence
<220> FEATURE:
<223> OTHER INFORMATION: Synthetic Construct

<400> SEQUENCE: 36

```
Met Tyr Gly Arg Arg Ala Arg Arg Arg Arg Ala Lys Thr Lys
 1               5                  10                  15
Gln Leu Arg Val Val Asn Gly Gly Gly Cys Asp Leu Pro Gln Thr
            20                  25                  30
His Ser Leu Gly Ser Arg Arg Thr Leu Met Leu Ala Gln Met Arg
        35                  40                  45
Arg Ile Ser Leu Phe Ser Cys Leu Lys Asp Arg His Asp Phe Gly Phe
 50                  55                  60
Pro Gln Glu Glu Phe Gly Asn Gln Phe Gln Lys Ala Glu Thr Ile Pro
 65                  70                  75                  80
Val Leu His Glu Met Ile Gln Gln Ile Phe Asn Leu Phe Ser Thr Lys
                 85                  90                  95
Asp Ser Ser Ala Ala Trp Asp Glu Thr Leu Leu Asp Lys Phe Tyr Thr
            100                 105                 110
Glu Leu Tyr Gln Gln Leu Asn Asp Leu Glu Ala Cys Val Ile Gln Gly
        115                 120                 125
Val Gly Val Thr Glu Thr Pro Leu Met Lys Glu Asp Ser Ile Leu Ala
130                 135                 140
Val Arg Lys Tyr Phe Gln Arg Ile Thr Leu Tyr Leu Lys Glu Lys Lys
145                 150                 155                 160
Tyr Ser Pro Cys Ala Trp Glu Val Val Arg Ala Glu Ile Met Arg Ser
                165                 170                 175
Phe Ser Leu Ser Thr Asn Leu Gln Glu Ser Leu Arg Ser Lys Glu
            180                 185                 190
```

<210> SEQ ID NO 37
<211> LENGTH: 33

-continued

```
<212> TYPE: PRT
<213> ORGANISM: Artificial Sequence
<220> FEATURE:
<223> OTHER INFORMATION: Synthetic Construct

<400> SEQUENCE: 37

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg

<210> SEQ ID NO 38
<211> LENGTH: 12
<212> TYPE: PRT
<213> ORGANISM: Artificial Sequence
<220> FEATURE:
<223> OTHER INFORMATION: Synthetic Construct

<400> SEQUENCE: 38

Ser Thr Asn Leu Gln Glu Ser Leu Arg Ser Lys Glu
1               5                   10
```